(12) United States Patent
Arata

(10) Patent No.: US 7,803,407 B2
(45) Date of Patent: *Sep. 28, 2010

(54) DISINFECTANT AND METHOD OF MAKING

(75) Inventor: Andrew B. Arata, Lake City, FL (US)

(73) Assignee: Pure Bioscience, El Cajon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/600,006

(22) Filed: Jun. 19, 2003

(65) Prior Publication Data

US 2005/0274624 A1    Dec. 15, 2005

Related U.S. Application Data

(62) Division of application No. 09/798,763, filed on Mar. 2, 2001, now Pat. No. 6,583,176, which is a division of application No. 09/169,229, filed on Oct. 9, 1998, now Pat. No. 6,197,814.

(60) Provisional application No. 60/061,673, filed on Oct. 10, 1997.

(51) Int. Cl.
- A01N 59/16 (2006.01)
- A01N 55/02 (2006.01)
- A01N 37/04 (2006.01)
- A61K 33/38 (2006.01)
- A61K 31/28 (2006.01)
- A61K 31/191 (2006.01)

(52) U.S. Cl. ............ 424/618; 424/DIG. 6; 514/495; 514/574; 514/709; 514/711; 514/724

(58) Field of Classification Search ............ 514/495, 514/553–574, 576, 578, 184, 709, 711, 724; 424/618, 619, DIG. 6; 422/22, 28; 205/440, 205/457

See application file for complete search history.

(56) References Cited

U.S. PATENT DOCUMENTS

| | | | |
|---|---|---|---|
| 2,510,510 A | 6/1950 | Mendenhall | |
| 2,658,072 A | 11/1953 | Kosmin | |
| 3,303,090 A | 2/1967 | Huffman et al. | |
| 3,422,183 A | 1/1969 | Ellison | |
| 3,600,186 A | 8/1971 | Mattson | |
| 3,647,439 A | 3/1972 | Bass | |
| 3,702,298 A | 11/1972 | Zsoldos | |
| 3,929,678 A | 12/1975 | Laughlin et al. | |
| 4,005,195 A | 1/1977 | Jandecek et al. | |
| 4,005,196 A | 1/1977 | Jandecek et al. | |
| 4,021,578 A | 5/1977 | Harich et al. | |
| 4,055,655 A | 10/1977 | Maurer et al. | |
| 4,180,473 A | 12/1979 | Maurer et al. | |
| 4,264,592 A | 4/1981 | Xhajanka | |
| 4,291,125 A | 9/1981 | Greatbatch | |
| 4,297,374 A | 10/1981 | Wess | |
| 4,385,632 A | 5/1983 | Odelhog | |
| 4,564,461 A | 1/1986 | Skold et al. | |
| 4,608,183 A | 8/1986 | Rossmoore | |
| 4,666,616 A | 5/1987 | Rossmoore | |
| 4,708,808 A | 11/1987 | Rossmoore | |
| 4,753,821 A | 6/1988 | Giesecke et al. | |
| 4,755,268 A | 7/1988 | Matsuo et al. | |
| 4,780,216 A | 10/1988 | Wojtowicz | |
| 4,797,300 A | 1/1989 | Jandacek et al. | |
| 4,889,844 A | 12/1989 | Silvetti, Sr. et al. | |
| 4,908,355 A | 3/1990 | Gettings et al. | |
| 4,915,955 A | 4/1990 | Gomori | |
| 4,933,178 A | 6/1990 | Capelli | |
| 5,011,681 A | 4/1991 | Ciotti et al. | |
| 5,017,295 A | 5/1991 | Antelman | |
| 5,063,062 A | 11/1991 | Greenspan et al. | |
| 5,073,382 A | 12/1991 | Antelman | |
| 5,078,902 A | 1/1992 | Antelman | |
| 5,081,106 A | 1/1992 | Bentley et al. | |
| 5,089,275 A | 2/1992 | Antelman | |
| 5,177,065 A | 1/1993 | Silvetti, Sr. et al. | |
| 5,236,698 A | 8/1993 | Richard et al. | |
| 5,306,514 A | 4/1994 | Letton | |
| 5,306,515 A | 4/1994 | Letton | |

(Continued)

FOREIGN PATENT DOCUMENTS

EP    0507691    10/1992

(Continued)

OTHER PUBLICATIONS

Srivastava, G.C. et al., "Development of ready to use antiseptic dressings—Part I . . . " Labdev J. Sci. Tech., vol. 8-B, No. 4, Oct. 1970, pp. 209-213.*

(Continued)

*Primary Examiner*—John Pak
(74) *Attorney, Agent, or Firm*—Morrison & Foerster LLP

(57) ABSTRACT

A non-toxic environmentally friendly aqueous disinfectant is disclosed for specific use as prevention against contamination by potentially pathogenic bacteria and virus. The aqueous disinfectant is formulated by electrolytically generating silver ions in water in combination with a citric acid. The aqueous disinfectant may include a suitable alcohol and/or a detergent. The aqueous disinfectant has been shown to be very effective at eliminating standard indicator organisms such as *staphylococcus aureus, salmonella cholerasuis* and *pseudomonas aeruginosa*.

8 Claims, 8 Drawing Sheets

U.S. PATENT DOCUMENTS

| | | | |
|---|---|---|---|
| 5,306,516 | A | 4/1994 | Letton |
| 5,332,511 | A | 7/1994 | Gay et al. |
| 5,332,568 | A | 7/1994 | Raspanti |
| 5,338,539 | A | 8/1994 | Raspanti |
| 5,362,714 | A | 11/1994 | Radford et al. |
| 5,364,649 | A | 11/1994 | Rossmoore et al. |
| 5,373,025 | A | 12/1994 | Gay |
| 5,382,337 | A | 1/1995 | Wlassics et al. |
| 5,464,559 | A | 11/1995 | Marchin et al. |
| 5,503,840 | A | 4/1996 | Jacobson et al. |
| 5,510,109 | A | 4/1996 | Tomioka et al. |
| 5,518,713 | A | 5/1996 | Raspanti |
| 5,520,906 | A | 5/1996 | Stein et al. |
| 5,601,811 | A | 2/1997 | Gallagher et al. |
| 5,660,840 | A | 8/1997 | Pruett |
| 5,736,591 | A | 4/1998 | Dunn |
| 5,820,918 | A | 10/1998 | Ronan et al. |
| 5,962,517 | A | 10/1999 | Murad |
| 6,017,461 | A | 1/2000 | Garvey et al. |
| 6,139,823 | A | 10/2000 | Drechsler et al. |
| 6,181,963 | B1 | 1/2001 | Chin et al. |
| 6,197,814 | B1 | 3/2001 | Arata |
| 6,294,186 | B1 | 9/2001 | Beerse et al. |
| 6,387,355 | B2 | 5/2002 | Heidenfelder et al. |
| 6,409,995 | B1 | 6/2002 | Habeck et al. |
| 6,478,946 | B1 | 11/2002 | Westwood |
| 6,583,176 | B2 | 6/2003 | Arata |
| 6,605,751 | B1 | 8/2003 | Gibbins et al. |
| 6,692,773 | B2 | 2/2004 | Burrell et al. |
| 6,838,095 | B2 * | 1/2005 | Newman et al. ............ 424/618 |
| 6,843,784 | B2 | 1/2005 | Modak et al. |
| 6,890,953 | B2 | 5/2005 | Arata |
| 7,026,308 | B1 | 4/2006 | Gavin et al. |
| 7,261,905 | B2 | 8/2007 | Arata |
| 2002/0016349 | A1 | 2/2002 | Heywang et al. |
| 2002/0192298 | A1 | 12/2002 | Burrell et al. |
| 2003/0198689 | A1 | 10/2003 | Arata |
| 2004/0044073 | A1 | 3/2004 | Arata |
| 2005/0202066 | A1 | 9/2005 | Arata |
| 2005/0245605 | A1 | 11/2005 | Arata |
| 2005/0247643 | A1 | 11/2005 | Arata |
| 2005/0274624 | A1 | 12/2005 | Arata |
| 2006/0051430 | A1 | 3/2006 | Arata et al. |
| 2006/0100273 | A1 | 5/2006 | Arata |
| 2006/0115440 | A1 | 6/2006 | Arata et al. |
| 2006/0188584 | A1 | 8/2006 | Arata et al. |
| 2007/0185350 | A1 | 8/2007 | Arata |
| 2007/0269530 | A1 | 11/2007 | Arata |

FOREIGN PATENT DOCUMENTS

| | | |
|---|---|---|
| EP | 0517104 | 12/1992 |
| EP | 0570838 | 11/1993 |
| EP | 0582189 | 2/1994 |
| EP | 0613893 | 9/1994 |
| EP | 0709080 | 5/1996 |
| EP | 1046391 | 10/2000 |
| EP | 1133980 | 9/2001 |
| EP | 1167358 | 1/2002 |
| GB | 1270410 | 4/1972 |
| GB | 2236117 | 3/1991 |
| JP | 47-32537 | 8/1972 |
| JP | 56-109584 | 8/1981 |
| JP | 62-163793 | 7/1987 |
| JP | 4-330007 | 11/1992 |
| JP | 06-320167 | 11/1994 |
| JP | 08-143746 | 6/1996 |
| JP | 08-164393 | 6/1996 |
| JP | 08-225418 | 9/1996 |
| JP | 08-268820 | 10/1996 |
| WO | WO-93/17002 | 9/1993 |
| WO | WO 96/28390 | 6/1996 |
| WO | WO-97/00851 | 1/1997 |
| WO | WO-99/18790 | 4/1999 |
| WO | WO-00/27390 | 5/2000 |
| WO | WO-2005/020915 | 3/2005 |
| WO | WO-2005/041861 | 5/2005 |
| WO | WO-2006/029213 | 3/2006 |

OTHER PUBLICATIONS

Dictionary of Organic Compounds. Chapman &Hall, London, 6$^{th}$ ed., vol. 2, p. 1552.*

Chemical Abstracts. 87:74283n Complexes of Silver (I) with Some Hydroxy Acids. Tsimbler, S. M.; Novikova, L.S. (USSR). Zh Neorg. Khim. 1977, 22 (7) 1842-6 (Russ).

Chemical Abstracts. 69.8964n Preservatives for Tobacco Paul Richli. Swiss 446691 (Cl. A 24b) Mar. 15, 1968, Appl. Apr. 22, 1964; 2pp.

Notice of Reason for Rejection for JP 2000-515434, issued Oct. 8, 2009, 3 pages.

Srivastava et al., Labdev. J. Sci. Tech. (1970) 8-B(4):209-214.

Baxter, "Evaluation of Axen® for Residual Activity," Nelson Laboratories, Inc., Salt Lake City, Utah, pp. 1-22 (Feb. 8, 2002).

Derwent Abstract, Accession No. 2000-268443, abstracting RU 2125971 [Feb. 10, 1999].

Derwent Abstract, Accession No. 2002-265533, abstracting RU 2179155 [Feb. 10, 2002].

IMS, "Axen® 30, Disinfectan, Fungicide & Virucide," Manufactured by ETI H2O, A Division of Innovative Medical Services, El Cajon, CA.

IMS, "IMS Announces Positive Research Results of Anti-Bacterial Acne Ingredient," Press Release, Innovative Medical Services, El Cajon, CA (Feb. 12, 2002).

Kawana et al., Dermatology (1997) 195(2):29-35.

Lin et al., "Experimental Results: Efficacy of Axenohol Solution in Eradicating *Legionella pneumophilal*," Special Pathogens Laboratory, VA Pittsburgh Healthcare System, Pittsburgh, PA 15240.

Mayer, "Accelerated Storage Stability of Axenohol and Axen," EPL Bio-Analytical Services, Inc., Harristown, Illinois, pp. 1-48 (May 8, 2000).

Miller, "Storage Stability of Axenohol and Axen Under Warehouse Conditions," EPL Bio-Analytical Services, Inc., Harristown, Illinois, pp. 1-71 (Aug. 10, 2001).

Moore, "Acute Dermal Toxicity Study in Rats—Limit Test," product safety labs, East Brunswick, New Jersey, pp. 1-14 (Oct. 21, 1999).

Moore, "Acute Oral Toxicity Study in Rats—Limit Test," product safety labs, East Brunswick, New Jersey, pp. 1-14 (Oct. 21, 1999).

Moore, "Dermal Sensitization Study in Guinea Pigs (Buehler Method)," product safety labs, East Brunswick, New Jersey, pp. 1-24 (Oct. 21, 1999).

Moore, "Primary Eye Irritation Study in Rabbits," product safetly labs, East Brunswick, New Jersey, pp. 1-15 (Oct. 6, 1999).

Moore, "Primary Eye Irritation Study in Rabbits," product safety labs, East Brunswick, New Jersey, pp. 1-15 (Oct. 21, 1999).

Moore, "Primary Skin Irritation Study in Rabbits," product safety labs, East Brunswick, New Jersey, pp. 1-15 (Oct. 21, 1999).

NLM, "PubChem Substance Summary," (PubChem Substance ID 679028) for "silver citrate," from the National Center for Biotechnology Information at the National Library of Medicine.

Product No. 006976, description of commercially available "silver citrate," from the online catalogue of Crescent Chemical Company, 1324 Motor Parkway, Islandia, New York 11749.

Product No. 3222, "silver citrate," from the online catalogue of ProChem, Inc., 826 Roosevelt Road, Rockford, IL 61109.

Vaughan, Cosmetics and Toiletries (1988) 103:47-69.

Yamamoto, "Electrochemical removal of discoloration on silver product surface," (Chemical Yamamoto K.K.) Kokai Tokkyo Koho JP 04,297,559 (92,297,599), [Chemical Abstracts 118:156836t; 1993].

Non-Final Office Action for U.S. Appl. No. 10/936,465, dated Jul. 5, 2006.

Amendment and Response for U.S. Appl. No. 10/936,465, dated Jan. 8, 2007.

Final Office Action for U.S. Appl. No. 10/936,465, dated Jun. 15, 2007.

Interview Summary for U.S. Appl. No. 10/936,465, dated Oct. 16, 2007.
Response and Amendment After Final for U.S. Appl. No. 10/936,465, dated Nov. 15, 2007.
Non-Final Office Action for U.S. Appl. No. 10/936,465, dated Jan. 9, 2008.
Response and Amendment for U.S. Appl. No. 10/936,465, dated Jul. 9, 2008.
Non-Final Office Action for U.S. Appl. No. 11/144,398, dated Jun. 29, 2006.
Amendment and Response for U.S. Appl. No. 11/144,398, dated Jan. 3, 2007.
Final Office Action for U.S. Appl. No. 11/144,398, dated Mar. 27, 2007.
Response and Amendment After Final for U.S. Appl. No. 11/144,398, dated Sep. 26, 2007.
Duty of Candor for U.S. Appl. No. 11/144,398, dated Oct. 4, 2007.
Interview Summary for U.S. Appl. No. 11/144,398, dated Oct. 16, 2007.
Supplemental Response and Amendment for U.S. Appl. No. 11/144,398, dated Dec. 10, 2007.
Non-Final Office Action for U.S. Appl. No. 11/144,398, dated Jan. 2, 2008.
Response and Amendment for U.S. Appl. No. 11/144,398, dated Jul. 1, 2008.
Non-Final Office Action for U.S. Appl. No. 10/232,499, dated Jan. 18, 2005.
Amendment for U.S. Appl. No. 10/232,499, dated Jul. 18, 2005.
Final Office Action for U.S. Appl. No. 10/232,499, dated Oct. 20, 2005.
Notice of Abandonment for U.S. Appl. No. 10/232,499, dated Apr. 28, 2006.
Examiner Interview Summary Record for U.S. Appl. No. 10/232,499, dated May 17, 2006.
Preliminary Amendment for U.S. Appl. No. 11/407,654, dated Apr. 20, 2006.
Preliminary Amendment for U.S. Appl. No. 11/407,654, dated Aug. 18, 2006.
Non-Final Rejection for U.S. Appl. No. 11/407,654, dated Jun. 20, 2008.
Abandonment for U.S. Appl. No. 11/407,654, dated Jan. 15, 2009.
Examiner Interview Summary Record for U.S. Appl. No. 11/407/654, dated Jan. 15, 2009.
Preliminary Amendment for U.S. Appl. No. 12/340,231, dated Dec. 19, 2008.
Interview Summary for U.S. Appl. No. 10/928,638, dated Nov. 18, 2005.
Non-Final Office Action for U.S. Appl. No. 10/928,638, dated Nov. 28, 2005.
Interview Summary for U.S. Appl. No. 10/928,638, dated Jun. 21, 2006.
Office Communication—Notice of Abandonment for U.S. Appl. No. 10/928,638, dated Jun. 28, 2006.
Non-Final Office Action for U.S. Appl. No. 10/928,639, dated Jul. 5, 2006.
Amendment and Response for U.S. Appl. No. 10/928,639, dated Jan. 8, 2007.
Final Office Action for U.S. Appl. No. 10/928,639, dated Jun. 15, 2007.
Interview Summary for U.S. Appl. No. 10/928,639, dated Oct. 16, 2007.
Response and Amendment After Final for U.S. Appl. No. 10/928,639, dated Nov. 19, 2007.
Non-Final Office Action for U.S. Appl. No. 10/928,639, dated Jan. 9, 2008.
Notice of Appeal Filed for U.S. Appl. No. 10/928,639, dated Jul. 9, 2008.
Applicant Arguments/Remarks Made in an Amendment for U.S. Appl. No. 10/928,639, dated Oct. 9, 2008.
Final Rejection for U.S. Appl. No. 10/928,639, dated Dec. 29, 2008.
Preliminary Amendment for U.S. Appl. No. 11/298,130, dated Dec. 8, 2005.
Non-Final Office Action for U.S. Appl. No. 11/298,130, dated Apr. 27, 2006.
Amendment and Election Under Restriction/Election Requirement for U.S. Appl. No. 11/298,130, dated Jul. 31, 2006.
Non-Final Office Action for U.S. Appl. No. 11/298,130, dated Sep. 27, 2006.
Office Communication—Notice of Abandonment for U.S. Appl. No. 11/298,130, dated Apr. 26, 2007.
Preliminary Amendment for U.S. Appl. No. 11/729,175, dated Mar. 27, 2007.
Preliminary Amendment for U.S. Appl. No. 11/729,175, dated May 15, 2007.
Non-Final Office Action for U.S. Appl. No. 11/729,175, dated Sep. 20, 2007.
Amendment/Req. Reconsideration—After Non-Final Rejection for U.S. Appl. No. 11/729,175, dated Mar. 19, 2008.
Final Rejection for U.S. Appl. No. 11/729,175, dated Jun. 17, 2008.
Applicant Arguments/Remarks Made in an Amendment for U.S. Appl. No. 11/729,175, dated Dec. 17, 2008.
Non-Final Office Action for U.S. Appl. No. 10/103,548, dated Jul. 1, 2003.
Interview Summary for U.S. Appl. No. 10/103,548, dated Aug. 26, 2003.
Amendment A for U.S. Appl. No. 10/103,548, dated Dec. 5, 2003.
Office Communication—Notice of Non-Compliant Amendment for U.S. Appl. No. 10/103,548, dated Dec. 24, 2003.
Amendment A—Corrected for U.S. Appl. No. 10/103,548, dated Jan. 26, 2004.
Final Office Action for U.S. Appl. No. 10/103,548, dated May 18, 2004.
Amendment for U.S. Appl. No. 10/103,548, dated Sep. 22, 2004.
Interview Summary for U.S. Appl. No. 10/103,548, dated Oct. 15, 2004.
Advisory Action for U.S. Appl. No. 10/103,548, dated Oct. 19, 2004.
Response Under 37 C.F.R. δ 1.116 for U.S. Appl. No. 10/103,548, dated Nov. 19, 2004.
Notice of Allowance for U.S. Appl. No. 10/103,548, dated Dec. 8, 2004.
Preliminary Amendment for U.S. Appl. No. 11/125,849, dated May 9, 2005.
Non-Final Office Action for U.S. Appl. No. 11/125,849, dated Aug. 1, 2006.
Amendment and Response for U.S. Appl. No. 11/125,849, dated Feb. 5, 2007.
Office Communication for U.S. Appl. No. 11/125,849, dated Apr. 19, 2007.
Amendment and Response for U.S. Appl. No. 11/125,849, dated Jun. 11, 2007.
Supplemental Response for U.S. Appl. No. 11/125,849, dated Aug. 27, 2007.
Duty of Candor for U.S. Appl. No. 11/125,849, dated Oct. 9, 2007.
Final Office Action for U.S. Appl. No. 11/125,849, dated Nov. 16, 2007.
Amendment and Response to Final Office Action and Request for Continued Examination for U.S. Appl. No. 11/125,849, dated May 15, 2008.
Non-Final Office Rejection for U.S. Appl. No. 11/125,849, dated Aug. 12, 2008.
Amendment/Req. Reconsideration After Non-Final Rejection, dated Feb. 12, 2009.
Office Communication—Restriction Requirement for U.S. Appl. No. 10/434,742, dated Nov. 19, 2003.
Election of Species for U.S. Appl. No. 10/434,742, dated Jan. 15, 2004.
Non-Final Office Action for U.S. Appl. No. 10/434,742, dated May 11, 2005.
Amendment for U.S. Appl. No. 10/434,742, dated Nov. 14, 2005.
Office Communication for U.S. Appl. No. 10/434,742, dated Feb. 7, 2006.
Response to Communication for U.S. Appl. No. 10/434,742, dated Aug. 4, 2006.
Final Office Action for U.S. Appl. No. 10/434,742, dated Oct. 20, 2006.

Amendment and Response After Final Office Action for U.S. Appl. No. 10/434,742, dated Mar. 23, 2007.
Notice of Allowance for U.S. Appl. No. 10/434,742, dated Apr. 19, 2007.
Issue Notification for U.S. Appl. No. 10/434,742, dated Aug. 28, 2007.
Preliminary Amendment for U.S. Appl. No. 11/832,474, dated Aug. 1, 2007.
Duty of Candor for U.S. Appl. No. 11/832,474, dated Oct. 3, 2007.
Interview Summary for U.S. Appl. No. 11/832,474, dated Oct. 15, 2007.
Non-Final Office Action for U.S. Appl. No. 10/600,006, dated Dec. 8, 2004.
Response to Restriction Requirement for U.S. Appl. No. 10/600,006, dated Jun. 7, 2005.
Non-Final Office Action for U.S. Appl. No. 10/600,006, dated Aug. 12, 2005.
Amendment for U.S. Appl. No. 10/600,006, dated Feb. 13, 2006.
Final Office Action for U.S. Appl. No. 10/600,006, dated Apr. 28, 2006.
Interview Summary for U.S. Appl. No. 10/600,006, dated May 6, 2006.
Amendment and Response to Office Action for U.S. Appl. No. 10/600,006, dated Mar. 27, 2007.
Non-Final Office Action for U.S. Appl. No. 10/600,006, dated Jun. 22, 2007.
Duty of Candor for U.S. Appl. No. 10/600,006, dated Oct. 9, 2007.
Interview Summary for U.S. Appl. No. 10/600,006, dated Oct. 15, 2007.
Amendment and Response to Office Action for U.S. Appl. No. 10/600,006, dated Dec. 26, 2007.
Final Office Action for U.S. Appl. No. 10/600,006, dated Apr. 1, 2008.
Notice of Appeal Filed for U.S. Appl. No. 10/600,006, dated Oct. 1, 2008.
Preliminary Amendment for U.S. Appl. No. 11/060,013, dated Feb. 16, 2005.
Requirement for Restrction/Election for U.S. Appl. No. 11/060,013, dated Jul. 31, 2006.
Response to Election/ Restriction Filed for U.S. Appl. No. 11/060,013, dated Dec. 4, 2006.
Amendment/Req. Reconsideration—After Non-Final Rejection for U.S. Appl. No. 11/060,013, dated Mar. 22, 2007.
Non-Final Rejection for U.S. Appl. No. 11/060,013, dated May 16, 2007.
Duty of Candor for U.S. Appl. No. 11/060,013, dated Oct. 3, 2007.
Examiner Interview Summary Record for U.S. Appl. No. 11/060,013, dated Oct. 16, 2007.
Amendment/Req. Reconsideration—After Non-Final Rejection for U.S. Appl. No. 11/060,013, dated Nov. 16, 2007.
Notice of Allowance and Fees Due for U.S. Appl. No. 11/060,013, dated Jan. 7, 2008.
Exmainer Interview Summary Record for U.S. Appl. No. 11/060,013, dated Jan. 2, 2008.
Notice of Allowance and Fees Due for U.S. Appl. No. 11/060,013, dated Jun. 4, 2008.
Issue Notification for U.S. Appl. No. 11/060,013, dated Oct. 14, 2008.
Preliminary Amendment for U.S. Appl. No. 12/204,374, dated Sep. 4, 2008.
Amended Claims for Chinese Patent Application No. 200580037477.6, dated Mar. 21, 2008.
Opposition filed by Gustavo M. Umana for Costa Rican Patent Application No. 9029, dated Oct. 27, 2008.
Office Action Response for Eurasian Patent Application No. 200700579, dated Nov. 13, 2008.
Office Action for Eurasian Patent Application No. 200700579, dated Apr. 24, 2008.
Response to Office Action for Mexican Patent Application No. MX/a/2007/002762, dated Jul. 10, 2007.
Written Opinion of the International Searching Authority for PCT/US2005/031876, dated Apr. 3, 2007.
International Preliminary Report on Patentability for PCT/US2005/031876, dated May 1, 2007.
Written Opinion for Singaporean Patent Application No. 200701618-1, dated Sep. 5, 2008.
Response to Written Opinion for Singaporean Patent Application No. 200701618-1, dated Feb. 5, 2009.
Office Action for Chinese Patent Application No. 200480024459.X, dated May 25, 2007.
Office Action Response for Chinese Patent Application No. 200480024459.X, dated Dec. 5, 2007.
Decision of Rejection for Chinese Patent Application No. 200480024459.X, dated Feb. 15, 2008.
Request for Reexamination for Chinese Patent Application No. 200480024459.X, dated May 30, 2008.
Office Action for Mexican Patent Application No. PA/a/2006/002283, dated Mar. 31, 2008.
Office Action Response for Mexican Patent Application No. PA/a/2006/002283, dated Aug. 6, 2008.
Office Action for Mexican Patent Application No. PA/a/2006/002283, dated Sep. 11, 2008.
Amendment for Mexican Patent Application No. PA/a/2006/002284, dated Jun. 27, 2007.
Office Action for New Zealand Patent Application No. 545932, dated May 15, 2008.
Office Action for New Zealand Patent Application No. 545933, dated May 20, 2008.
International Search/Written Opinion for PCT/US2004/027901, dated Sep. 8, 2005.
International Preliminary Report on Patentability for PCT/US2004/027901, dated Feb. 28, 2006.
Notification of Grant for Singaporean Patent Application No. 200601193-6, dated Dec. 31, 2008.
Certificate of Grant of Patent for Singaporean Patent Application No. 200601197-7, dated Sep. 30, 2008.
Patent Certificate for South African Patent Application No. 2006/02542, Sep. 26, 2007.
Patent Certificate for South African Patent Application No. 2006/02543, dated Mar. 26, 2008.
Examination for ARIPO Patent Application No. AP/P/00/01783, dated Mar. 17, 2003.
Grant of Patent for ARIPO Patent Application No. AP/P/00/01783, dated Jun. 30, 2005.
Examination for Australian Patent Application No. 11880/99, dated Dec. 5, 2000.
Response to Examination for Australian Patent Application No. 11880/99, dated Aug. 12, 2002.
First Office Action for Canadian Patent Application No. 2305139, dated Jun. 13, 2006.
Amendment/Remarks After Examiner's Report for Canadian Patent Application No. 2305139, dated Dec. 13, 2006.
Office Action for Canadian Patent Application No. 2305139, dated May 14, 2007.
Amendment/Remarks After Examiner's Report for Canadian Patent Application No. 2305139, dated Nov. 14, 2007.
Notice of Allowance for Canadian Patent Application No. 2305139, dated Feb. 25, 2008.
First Office Action for Chinese Patent Application No. 98812103.4, dated Aug. 22, 2003.
Response to First Office Action for Chinese Patent Application No. 98812103.4, dated Mar. 4, 2004.
Second Office Action for Chinese Patent Application No. 98812103.4, dated May 14, 2004.
Response to Second Office Action for Chinese Patent Application No. 98812103.4, dated Sep. 27, 2004.
Third Office Action for Chinese Patent Application No. 98812103.4, Feb. 25, 2005.
Response to Third Office Action for Chinese Patent Application No. 98812103.4, dated Jul. 12, 2005.
Fourth Office Action for Chinese Patent Application No. 98812103.4, dated Dec. 9, 2005.
Response to Fourth Office Action for Chinese Patent Application No. 98812103.4, dated Apr. 21, 2006.

Decision on Rejection for Chinese Patent Application No. 98812103.4, dated Jan. 19, 2007.
Request for Examination for Chinese Patent Application No. 98812103.4, dated May 8, 2007.
Notice of Reexamination for Chinese Patent Application No. 98812103.4, dated Jul. 4, 2008.
Response to Reexamination for Chinese Patent Application No. 98812103.4, dated Oct. 20, 2008.
Rejection Reversed for Chinese Patent Application No. 98812103.4, dated Dec. 23, 2008.
First Office Action for Chinese Patent Application No. 200410045711.7, dated Jun. 10, 2005.
Decision on Rejection for Chinese Patent Application No. 200410045711.7, dated Jun. 9, 2006.
Response to Decision on Rejection for Chinese Patent Application No. 200410045711.7, dated Sep. 20, 2006.
Reexamination Decision for Chinese Patent Application No. 200410045711.7, dated Oct. 22, 2008.
Decision on Grant for Chinese Patent Application No. 200410045711.7, dated Feb. 6, 2009.
First Office Action for Chinese Patent Application No. 200410045710.2, dated Aug. 18, 2006.
First Office Action for Chinese Patent Application No. 200410045709.X, dated Jun. 29, 2005.
Decision to Grant for Chinese Patent Application No. 200410045709.X, dated Sep. 1, 2006.
Granted Claims in English for Chinese Patent Application No. 200410045709.X, dated Sep. 1, 2006.
International Preliminary Exam Report for European Patent Application No. 98954966.2, dated Jun. 9, 2000.
First Exam Report for European Patent Application No. 98954966.2, dated Jul. 24, 2006.
Response to Exam for European Patent Application No. 98954966.2, dated Jan. 30, 2007.
Notice of Allowance for European Patent Application No. 98954966.2, dated Apr. 10, 2004.
Decision to Grant for European Patent Application No. 98954966.2, dated Nov. 8, 2007.
Notice of Opposition for European Patent Application No. 98954966.2, dated Sep. 10, 2008.
Examination Report for New Zealand Patent Application No. 503582, dated May 13, 2002.
Examination Report for New Zealand Patent Application No. 503582, dated Sep. 6, 2002.
Grant of Patent for New Zealand Patent Application No. 503582, dated Mar. 31, 2003.
Grant of Patent for New Zealand Patent Application No. 518845, dated Jun. 8, 2004.
Written Opinion for PCT/US98/21604, dated Oct. 27, 1999.
International Preliminary Exam Report for PCT/US98/21604, dated Mar. 22, 2000.
Office Action for Brazilian Patent Application No. 9813857-0, mailed on Feb. 25, 2009, 4 pages.

* cited by examiner

INITIAL INTERVAL SHELF-LIFE TEST

|  | 1% Citric Acid | | | 10% Citric Acid | | |
|---|---|---|---|---|---|---|
|  | 3 ppm | 30 ppm | 300 ppm | 3 ppm | 30 ppm | 300 ppm |
| Week 1 | 1.006 | 9.630 | 2.060 | 0.676 | 0.690 | 145.94 |
|  | 0.983 | 9.925 | 1.960 | 0.434 | 1.010 | 157.32 |
|  | 1.174 | 9.765 | 1.490 | 0.688 | 0.865 | 165.34 |
| Avg. | 1.054 | 9.773 | 1.837 | 0.599 | 0.855 | 156.20 |
| Week 2 | 0.877 | 0.455 | <0.050 | 0.858 | 4.580 | 158.62 |
|  | 0.649 | 0.310 | <0.050 | 0.950 | 4.635 | 157.10 |
|  | 0.738 | 0.290 | <0.050 | 0.870 | 4.765 | 159.18 |
| Avg. | 0.755 | 0.352 | <0.050 | 0.893 | 4.660 | 158.30 |
| Week 3 | 0.630 | 0.925 | 2.690 | 1.140 | 15.060 | 160.62 |
|  | 0.688 | 2.150 | 6.600 | 1.230 | 27.025 | 163.44 |
|  | 0.666 | 3.380 | 0.110 | 1.370 | 26.605 | 158.68 |
| Avg. | 0.661 | 2.152 | 3.133 | 1.247 | 22.897 | 160.91 |
| Week 4 | 0.624 | 2.115 | 1.260 | 3.094 | 3.355 | 151.82 |
|  | 0.652 | 0.850 | 8.830 | 2.094 | 4.865 | 163.10 |
|  | 0.600 | 1.055 | 0.140 | 2.582 | 7.975 | 169.96 |
| Avg. | 0.625 | 1.340 | 1.743 | 2.590 | 5.398 | 161.63 |

FIG. 5

SECONDARY INTERVAL SHELF-LIFE TEST

|  | 1.0% Citr Acid | 5.0% citric Acid | 10% Citric Acid |
|---|---|---|---|
| Week 0 | 772.0 mg/L | 282.0 mg/L | 678.0 mg/L |
| Week 7 | 143.3 mg/L | 359.2 mg/L | 824.6 mg/L |
| Week 14 | 139.8 mg/L | 359.6 mg/L | 842.5 mg/L |
|  | 143.6 mg/L | 355.9 mg/L | 822.0 mg/L |
|  | 140.5 mg/L | 358.2 mg/L | 817.3 mg/L |
| Mean | 141.3 mg/L | 357.9 mg/L | 827.3 mg/L |
| Week 21 | 1.063 mg/L | 350.2 mg/L | 982.9 mg/L |
|  | 1.022 mg/L | 335.0 mg/L | 1019.4 mg/L |
|  | 1.066 mg/L | 331.0 mg/L | 1017.3 mg/L |
|  | 1.050 MYLL | 338.7 mg/L | 1006.5 mg/L |

FIG. 6

EFFICACY AGAINST SALMONELLA CHOLERASUIS

| Sample | 15 sec. | 1 Minute | 5 Minutes | 10 minutes | 30 minutes |
|---|---|---|---|---|---|
| Ethanol 20% (a) | 1.93E+06 | 7.10E+05 | 5.20E+03 | 2.00E+02 | 1.00E+02 |
| Ethanol 20% (b) | 2.38E+06 | 1.02E+06 | 7.10E+03 | 3.00E+02 | 1.00E+02 |
| Ethanol 20% (c) | 1.66E+06 | 6.70E+05 | 8.90E+03 | 1.00E+02 | 1.00E+02 |
| Ethacol 20% (d) | 1.95E+06 | 6.70E+05 | 8.50E+03 | 1.00E+02 | 1.00E+02 |
| Average | 1.98E+06 | 7.68E+05 | 7.43E+03 | 1.75E+02 | 1.00E+02 |
| % Reduction | 81.3208 | 92.7594 | 99.9300 | 99.9983 | 99.9991 |
| | | | | | |
| Ag Citric Acid & ETOH (a) | 6.00E+03 | 1.00E+01 | 1.00E+01 | 1.00E+01 | 1.00E+01 |
| Ag Citric Acid & ETOH (b) | 6.80E+03 | 1.00E+01 | 1.00E+01 | 1.00E+01 | 1.00E+01 |
| Ag Citric Acid & ETOH (c) | 5.27E+03 | 1.00E+01 | 1.00E+01 | 1.00E+01 | 1.00E+01 |
| Ag Citric Acid & ETOH (d) | 4.81E+03 | 1.00E+01 | 1.00E+01 | 1.00E+01 | 1.00E+01 |
| Average | 5.72E+03 | 1.00E+01 | 1.00E+01 | 1.00E+01 | 1.00E+01 |
| % Reduction | 99.9460 | 99.9999 | 99.9999 | 99.9999 | 99.9999 |
| | | | | | |
| Citric Acid (a) | | 1.35E+06 | 8.00E+01 | 1.00E+01 | 1.00E+01 |
| Citric Acid (b) | | 1.22E+06 | 5.00E+01 | 1.00E+01 | 1.00E+01 |
| Citric Acid (c) | | 1.00E+06 | 1.00E+02 | 1.00E+01 | 1.00E+01 |
| Citric Acid (d) | | 1.27E+06 | 7.00E+01 | 1.00E+01 | 1.00E+01 |
| Average | | 1.21E+06 | 7.50E+01 | 1.00E+01 | 1.00E+01 |
| % Reduction | | 88.5849 | 99.9993 | 99.9999 | 99.9999 |
| Inoculum (a) | | | | 7.30E+06 | |
| Inoculum (b) | | | | 1.39E+07 | |
| Average | | | | 1.06E+07 | |

FIG. 7

EFFICACY AGAINST STAPHYLOCOCCUS AUREUS

| Sample | 15 sec. | 1 Minute | 5 Minutes | 10 minutes | 30 minutes |
|---|---|---|---|---|---|
| Ethanol 20% (a) | 4.29E+06 | 9.30E+06 | 6.80E+06 | 9.30E+06 | 7.20E+06 |
| Ethanol 20% (b) | 9.30E+06 | 8.40E+06 | 9.70E+06 | 8.40E+06 | 1.06E+07 |
| Ethanol 20% (c) | 1.06E+07 | 8.20E+06 | 7.40E+06 | 8.30E+06 | 8.50E+06 |
| Ethanol 20% (d) | 1.00E+07 | 8.20E+06 | 8.10E+06 | 8.50E+06 | 1.23E+07 |
| Average | 8.55E+06 | 8.53E+06 | 8.10E+06 | 8.63E+06 | 9.65E+06 |
| % Reduction | 37.8364 | 38.0000 | 41.8182 | 37.2727 | 29.8182 |
| | | | | | |
| Ag Citric Acid & Ethanol (a) | 2.54E+06 | 5.51E+04 | 1.00E+01 | 1.00E+01 | 1.00E+01 |
| Ag Citric Acid & Ethanol (b) | 2.67E+06 | 2.50E+04 | 1.00E+01 | 1.00E+01 | 1.00E+01 |
| Ag Citric Acid & Ethanol (c) | 6.83E+06 | 8.00E+04 | 1.00E+01 | 1.00E+01 | 1.00E+01 |
| Ag Citric Acid & Ethanol (d) | 4.46E+06 | 8.10E+04 | 1.00E+01 | 1.00E+01 | 1.00E+01 |
| Average | 4.13E+06 | 6.03E+04 | 1.00E+01 | 1.00E+01 | 1.00E+01 |
| % Reduction | 70.0000 | 99.5616 | 99.999 | 99.9999 | 99.9999 |
| | | | | | |
| Ag Citric Acid (a) | | 6.99E+06 | 1.06E+06 | 9.10E+03 | 1.00E+01 |
| Ag Citric Acid (b) | | 5.50E+06 | 6.90E+05 | 8.30E+03 | 1.00E+01 |
| Ag Citric Acid (c) | | 7.31E+06 | 8.00E+05 | 1.89E+04 | 1.00E+01 |
| Ag Citric Acid (d) | | 5.87E+06 | 9.70E+05 | 1.66E+04 | 1.00E+01 |
| Average | | 6.42E+06 | 8.80E+05 | 1.32E+04 | 1.00E+01 |
| % Reduction | | 53.3271 | 93.6000 | 99.9038 | 99.9999 |
| | | | | | |
| Citric Acid (a) | | 7.10E+06 | 1.06E+07 | 1.17E+07 | 1.13E+07 |
| Citric Acid (b) | | 8.20E+06 | 9.70E+06 | 1.18E+07 | 7.40E+06 |
| Citric Acid (c) | | 1.05E+07 | 8.60E+06 | 6.70E+06 | 2.80E+06 |
| Citric Acid (d) | | 6.00E+06 | 9.60E+06 | 7.30E+06 | 1.06E+07 |
| Average | | 7.95E+06 | 9.63E+06 | 9.38E+06 | 8.03E+06 |
| % Reduction | | 42.1818 | 30.0000 | 31.8182 | 41.6364 |
| Inoculum (a) | | | 1.41E+07 | | |
| Inoculum (b) | | | 1.34E+07 | | |
| Average | | | 1.38E+07 | | |

FIG. 8

EFFICACY AGAINST PSEUDOMONAS AERUGINOSA

| Sample | 15 sec. | 1 min. | 5 mins. | 10 mins. | 30 mins. |
|---|---|---|---|---|---|
| Ethanol 20% (a) | 2.85E+06 | 2.95E+06 | 8.10E+06 | 3.70E+06 | 2.30E+06 |
| Ethanol 20% (b) | 3.26E+06 | 2.90E+06 | 7.30E+06 | 3.90E+06 | 2.25E+06 |
| Ethanol 20% (c) | 2.37E+06 | 2.50E+06 | 6.70E+06 | 3.14E+06 | 5.70E+06 |
| Ethanol 20% (d) | 2.55E+06 | 2.50E+06 | 7.50E+06 | 3.00E+06 | 6.90E+06 |
| Average | 2.76E+06 | 2.71E+06 | 7.40E+06 | 3.44E+06 | 4.29E+06 |
| % Reduction | 66.9760 | 67.5150 | 11.3772 | 58.8623 | 48.6527 |
| | | | | | |
| Ag citric Acid & ETOH (a) | 9.60E+05 | 1.58E+04 | 1.00E+01 | 1.00E+01 | 1.00E+01 |
| Ag Citric Acid & ETOH (b) | 1.27E+06 | 1.43E+04 | 1.00E+01 | 1.00E+01 | 1.00E+01 |
| Ag Citric Acid & ETOH (c) | 1.58E+06 | 1.40E+04 | 1.00E+01 | 3.00E+01 | 1.00E+01 |
| Ag Citric Acid & ETOH (d) | 1.43E+04 | 1.41E+04 | 1.00E+01 | 5.00E+01 | 1.00E+01 |
| Average | 9.56E+05 | 1.46E+04 | 1.00E+01 | 2.50E+01 | 1.00E+01 |
| % Reduction | 88.5500 | 99.8257 | 99.9999 | 99.9997 | 99.9999 |
| Ag Citric Acid (a) | | 3.17E+06 | 9.10E+05 | 1.51E+04 | 1.00E+01 |
| Ag Citric Acid (b) | | 2.55E+06 | 1.38E+06 | 2.22E+04 | 1.00E+01 |
| Ag Citric Acid (c) | | 3.08E+06 | 1.13E+06 | 3.91E+04 | Lost count |
| Ag Citric Acid (d) | | 2.64E+06 | 1.03E+06 | 3.17E+04 | 3.00E+01 |
| Average | | 2.86E+06 | 1.11E+06 | 2.70E+04 | 1.67E+01 |
| % Reduction | | 65.7485 | 86.6766 | 99.6763 | 99.9998 |
| | | | | | |
| Citric Acid (a) | | 7.90E+06 | 3.03E+06 | 7.30E+06 | 7.50E+06 |
| Citric Acid (b) | | 6.90E+06 | 2.70E+06 | 7.70E+06 | 2.90E+06 |
| Citric Acid (c) | | 1.29E+07 | 2.88E+07 | 2.22E+06 | 6.10E+06 |
| Citric Acid (d) | | 1.00E+07 | 2.72E+07 | 7.90E+06 | 2.80E+06 |
| Average | | 9.43E+06 | 1.54E+07 | 6.28E+06 | 4.83E+06 |
| % Reduction | | -12.8743 | -84.8204 | 24.7904 | 42.2156 |
| Inoculum (a) | | | 7.80E+06 | | |
| Inoculum (b) | | | 8.90E+06 | | |
| Average | | | 8.35E+06 | | |

FIG. 9

DISINFECTANT AND METHOD OF MAKING

This application is a divisional of application Ser. No. 09/798,763 filed Mar. 2, 2001, now U.S. Pat. No. 6,583,176 the disclosure of which is incorporated herein by reference. Divisional application Ser. No. 09/798,763 filed Mar. 2, 2001 is a divisional application of application Ser. No. 09/169,229 filed Oct. 9, 1998, now U.S. Pat. No. 6,197,814 issued Mar. 6, 2001. Application Ser. No. 09/169,229 filed Oct. 9, 1998 claims priority to provisional application Ser. No. 60/061,673 filed Oct. 10, 1997. All subject matter set forth in application Ser. No. 09/798,763 and application Ser. No. 09/169,229 and application Ser. No. 60/061,673 are incorporated by reference into the present application

BACKGROUND OF THE INVENTION

1. Field of the Invention

This invention relates to disinfectants and more particularly to an environmentally friendly, non-toxic aqueous disinfectant for specific use against pathogenic bacteria and viruses.

2. Background of the Invention

The prior art has demonstrated that the presence of copper and silver ions in an aqueous solution is useful as a disinfectant. Many in the prior art have used copper and silver ions in an aqueous solution as a disinfectant in water systems such as cooling towers, swimming pools, hot water systems in hospitals, potable water systems, spa pools and the like.

Typically, copper and silver electrodes were connected to a direct current power supply. When the direct current was applied to the copper and silver electrodes, copper and silver ions were generated by an electrolysis process from the copper and silver ions within the water. In one example of the prior art, water was passed continuously through an ion chamber having copper and silver electrodes. The water emanating from the ion chamber contained the copper and silver ions generated by copper and silver electrodes within the ion chamber. The water emanating from the ion chamber containing the copper and silver ions was used as a disinfectant in water systems such as cooling towers, swimming pools, hot water systems in hospitals, potable water systems, spa pools and the like. The copper and silver ions within the water systems acted as a disinfectant for controlling algae, viruses, bacteria and the like.

U.S. Pat. No. 3,422,183 to Ellison discloses biocide compositions comprising ultra-violet irradiated silver fluoride solutions containing colloidal silver resulting from the irradiation and kept in dispersion by a protective colloid, e.g., casein or gelatin, and biocide uses thereof in sline control, against pathogens or other microbes in food or beverage containers or processing equipment, as an ingredient of wood preservatives, as a bactericide in paints, as a biocide in synthetic polymer films, as a sterilant in bandages, and biocide-like uses in other areas.

U.S. Pat. No. 3,702,298 to Zsoldos discloses a method of maintaining a highly oxidizing aqueous solution intended primarily for treatment of swimming pool water. A metal having a multiple valence is interacted to a lower valence with oxidizable debris in the solution, and the metal is continuously re-oxidized to a higher valence by maintaining in the water a constant excess of an oxidizer bank consisting of a salt of a peroxy acid. Silver, copper and nickel are suitable metals and their salts have germicidal properties which are greatly increased and the spectrum broadened by converting the mono salt to a divalent or trivalent salt.

U.S. Pat. No. 4,180,473 to Maurer et al. discloses a method of transporting metal ions by introducing a metal complex into a medium containing a moiety which demands the metal ion and the complex releases the ions in a controlled manner upon demand. The metal complexes have an aqueous proton induced dissociation property represented by a sigmoidally-shaped curve on a Cartesian coordinate plot of the negative log of the metal ion concentration versus the negative log of hydrogen ion concentration. This dissociation property causes a controlled release of metal ion into mediums containing a reacting moiety upon demand for the metal ion. For example, metal working emulsions of oil and water are stabilized by the addition thereto of minor amounts of a metal complex, e.g. disodium monocopper (II) citrate, which at alkaline pH metalworking conditions above about 7 to about 9 releases metal catons to the emulsions imparting stabilizing characteristics which prevent emulsion degradation by a number of factors commonly encountered in metalworking operations. Also, the method is effective in the controlled release of metal ions in the normal range of physiological pH, i.e. about 4 to 9, for growth controlling action against microorganisms including bacteria, fungi and viruses.

U.S. Pat. No. 4,291,125 to Greatbatch discloses a method and apparatus for killing plant and animal bacteria and plant viroids by electrically generated silver ions. The silver ions serve as germicidal agents in infection control and are generated by very slow electrical anodic corrosion of a silver wire located closely adjacent the infection site. In particular, a silver anode and a cathode of non-corroding metal are located in an electrolytic nutrient medium with the silver anode being within five millimeters of the infection site, and a direct voltage is applied to the anode and cathode in a manner passing a positive current in the microampere range into the silver anode causing it to corrode slightly and give off silver ions which produce a germicidal environment about the infection site.

U.S. Pat. No. 4,385,632 to Odelhog discloses an absorbent body for collecting blood, feces and urine containing a water-soluble copper salt which impedes bacterial growth, prevents the breaking-down of urea into ammonia and complex-binds ammonia so as to prevent the occurrence of unpleasant odor. Preferably copper acetate is used, in which even the acetate ion has germicidal effect.

U.S. Pat. No. 4,564,461 to Skold et al. discloses mechanical working of cast iron performed in the presence of an aqueous metal working composition containing an organic copper (II) complex and an iron corrosion inhibitor. An aqueous concentrate, which after dilution with water is suitable for application in mechanical working of cast iron, contains 1-50% copper (II) complex with such a $Cu_2+$ content of 0.5-20%, 1-50% iron corrosion inhibitor, 0-50% lubricant, 0-20% pH-regulators, bactericides and solubilizing agents and 10-70% water.

U.S. Pat. No. 4,608,183 to Rossmoore discloses antimicrobial mixtures of isothiazolones and a metal complex with a polyfunctional ligand which are synergistic. The mixtures particularly include mixtures of a monocopper disodium citrate as the ligand and a 5-x-2-lower alkyl 4-isothiazolin-3-one wherein x is a halo or hydrogen group as the isothiazolone. The compositions are particularly useful for metal cutting fluids wherein long duration antimicrobial activity is desired.

U.S. Pat. No. 4,666,616 to Rossmoore discloses synergistic anti-microbial compositions containing a mixture of a metal complex of a polyfunctional organic liquid and a biocidal composition which contains or releases a lower aldehyde containing 1 to 5 carbon atoms. The compositions are particularly useful as metal working fluids at alkaline pH and have a broad spectrum of activity against fungi and bacterial.

U.S. Pat. No. 4,708,808 to Rossmoore discloses synergistic anti-mircrobial compositions containing a mixture of a metal complex of a polyfunctional organic ligand and a biocidal composition which contains or releases a lower aldehyde containing 1 to 5 carbon atoms. The compositions are particularly useful as metal working fluids at alkaline pH and have a broad spectrum of activity against fungi and bacteria.

U.S. Pat. No. 4,780,216 to Wojtowicz discloses a sanitizing composition consisting essentially of a mixture of a calcium hypochlorite compound and a peroxydisulfate compound having the formula: $M_xS_2O_8$ where M is an alkali metal or alkaline earth metal, and x is 1 or 2 is employed in treating water to improve pH control and provide increased removal of organic materials. The compositions provide improved sanitation of water in swimming pools, spas, and cooling towers by efficiently oxidizing organic impurities while helping to minimize the increase in the pH of the water. This permits a reduction in the amount and frequency of addition of acidic compounds such as hydrochloric acid to the water bodies. Further, the incorporation of additives such as algaecides, dispersant, and clarifying agents provides for significant improvements in water quality as evidenced by sparkling pure water.

U.S. Pat. No. 4,915,955 to Gomori discloses a concentrate with an unlimited shelf-life, which can be mixed with hydrogen peroxide at a ratio of 1:99 to 1:199 to become an effective disinfectant, is obtained when a viscous solution of inorganic acid, with a pH less than or equal to 1.6, is mixed with a silver salt compound or a colloidal silver compound at 50° to 66° C. The mixture is further combined at room temperature with other inorganic acid(s) to reach a total of 100 g inorganic acid(s) per liter of water at room temperature, an organic acid stabilizer is added and the mixture is homogenized. The concentrate, during storage, remains homogeneous and crystal-clear.

U.S. Pat. No. 4,933,178 to Capelli discloses a medical device with an antimicrobial coating that is safe, effective, photostable and readily manufacturable produced by applying a composition to at least one body fluid-contacting surface of the device such that a solid coating is provided on that surface, the coating composition comprising an oligodynamic metal salt of a sulfonylurea, a polymeric material, at least one acid compound selected from the group consisting of a water-soluble carboxylic acid and water-insoluble carboxylic acid, and a carrier liquid in which foregoing components are soluble. The antimicrobial coating accommodates variation in the release of antimicrobial metal ions as a function of the intended use for a medical device to which the coating is applied.

U.S. Pat. No. 5,017,295 to Antelman discloses a method or methods of controlling the growth of bacteria in the water of swimming pools and/or industrial water supplies by adding to the water a specified concentration of a stable divalent silver compound. The invention has the advantage over chlorination in that it is odorless and non-volatile. It furthermore is superior to monovalent silver compounds as these compounds do not decompose in the presence of light and resist precipitation by halides and form divalent soluble complexes which in the monovalent state are invariably insoluble solids.

U.S. Pat. No. 5,073,382 to Antelman discloses a solid alkaline bactericidal compositions suitable for compounding alkaline end products such as food and dairy cleaners and surgical scrubbing soaps, formed by the neutralization of acid stabilized inorganic divalent silver complexes and capable of effecting 100% kills upon cultures of anaerobic bacteria colonies of 100K/cc. within 5 minutes.

U.S. Pat. No. 5,078,902 to Antelman discloses divalent silver halides providing a source for divalent bactericidal silver ions in the presence of persulfate. The halides are especially effective when applied to water used in industrial cooling installations, hot tubs and swimming pools and will conform to stringent EPA requirements for waters utilized for bathing as in tubs and pools of 100% kills of 100 K/cc *E. Coli* coliforms within 10 minutes, exemplary of which are the chloride and bromide which give 100% kills within 5 minutes. The halides, of course, can be used in salty water since they are solids immune from halide action that would otherwise precipitate soluble divalent silver from solution.

U.S. Pat. No. 5,089,275 discloses solid bactericidal compositions based on divalent silver (Ag(II)) as the active sanitized agent. The compositions are prepared by reacting acid liquid Ag(II) complexes with anhydrous calcium sulfate so as to form a solid matrix in which the bactericide is entrapped in the resulting hydrated calcium sulfate. Optimum compositions are described consisting of Ag(II) of solid (by weight) to liquid (by volume) is 5:2. The resulting solid bactericides can be used in water cooling installations. They are capable of causing 100% kills within 10 minutes of *E. Coli* conforms in conformity with EPA protocols, allowing them to qualify as swimming pool and hot tub sanitizers. Since the compositions are based on calcium sulfate, they are also suitable as mineralizers, thus providing a dual function.

U.S. Pat. No. 5,332,511 to Gay et al. discloses a process for sanitizing water in swimming pools, spas and hot tubs whereby the level of bacteria in said water is lowered comprising treating said water with a bactericidal effective amount of a combination of diisodecyl dimethyl ammonium chloride and copper (II) ions, the concentration of diisodecyl dimethyl ammonium chloride in said water being less than about 60 parts per million parts of water by weight and treating said water at least intermittently with an oxidant selected from the group consisting of available chlorine and ozone.

U.S. Pat. No. 5,364,649 to Rossmoore et al. discloses activity of antimicrobial compounds selected from isothiazolones and compounds which release formaldehyde enhanced with a metal complex of a lower alkanolamine, particularly copper (cupric) trietha-iolamine. The enhancement is particularly useful in metalworking fluids.

U.S. Pat. No. 5,373,025 to Gay discloses a sanitizer composition comprising a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; and (b) a copper (II) ion source.

U.S. Pat. No. 5,382,337 to Wlassics et al. discloses a process for oxidizing organic materials or compounds in aqueous phase, with hydrogen peroxide and in the presence of ferrous ions FE-(II), and optionally cupric ions cu-(II), carried out under irradiation with artificial visible light.

U.S. Pat. No. 5,464,559 to Marchin et al. discloses a composition provided for treating drinking water for disinfecting and/or removing iodide. The composition utilizes resin bound silver ions. For performing the disinfection or iodide removal with minimal release of silver ions into the water being treated, a chelating resin having iminodiacetate chelating groups is employed, and the resin is loaded with not over 0.5 mole of silver ions per mole of iminodiacetate.

U.S. Pat. No. 5,503,840 to Jacobson et al. discloses an antimicrobial composition of titanium dioxide, barium sulfate, zinc oxide particles, and mixtures thereof having successive coatings of silver, in some cases a coating of zinc and/or copper compounds such as zinc oxide, copper (II) oxide and zinc silicate; silicon dioxide; alumina; and a dispersion aid such as dioctyl azelate.

U.S. Pat. No. 5,510,109 to Tomioka et al discloses an antibacterial and antifungal composition which comprises an antibacterial and antifungal material carried on a porous particle carrier. Preferably, the porous particle carrier is a silica gel particle. The antibacterial and antifungal material is at least one metal complex salt, and can contain plant extracts and the like in addition to the metal complex salt. At least a portion of the surface of the above-mentioned carrier having the antibacterial and antifungal composition can be coated with a coating material.

Unfortunately, these copper and silver ions within an aqueous solution have only a limited stable ionic life. After a limited time, the copper and silver ions form complexes with other elements thus diminishing the concentration of the copper and silver ions within the aqueous solution. Accordingly, the aqueous solution had to be replenished with copper and silver ions to maintain the concentration of the copper and silver ions within the aqueous solution. The aqueous solution may be replenished with copper and silver ions by constantly circulating the aqueous solution thorough the ion chamber.

The present invention provides an aqueous disinfectant solution having a stable ionic form having an extended useful shelf-life. The extended useful shelf-life of the aqueous disinfectant solution enables the aqueous disinfectant solution to be packaged in an aqueous concentrate form.

Therefore, it is an object of the present invention to provide an improved disinfectant and the method of making comprising an aqueous disinfectant for specific use as prevention against contamination by potentially pathogenic bacteria and virus and antifungal properties.

Another object of this invention is to provide an improved disinfectant and the method of making which is an effective disinfectant for eliminating standard indicator organisms such as *staphylococcus aureus, salmonella cholerasuis* and *pseudomonas aeruginosa*.

Another object of this invention is to provide an improved disinfectant and the method of making which is a non-toxic, environmentally friendly aqueous disinfectant.

Another object of this invention is to provide an improved disinfectant and the method of making which comprises a stable ionic formulation having an extended useful shelf-life.

Another object of this invention is to provide an improved disinfectant and the method of making which may be packaged in a concentrated aqueous form.

Another object of this invention is to provide an improved disinfectant and the method of making which may be electrolytically generated in a batch process or a continuous process.

Another object of this invention is to provide an improved disinfectant and the method of making which is electrolytically generated in an economical manner.

Another object of this invention is to provide an improved disinfectant and the method of making which is suitable for use with an alcohol and/or a detergent.

Another object of this invention is to provide an improved disinfectant and the method of making which may be used on exposed and/or contaminated surfaces to kill bacteria, virus, fungi and other micro-organisms.

Another object of this invention is to provide an improved disinfectant and the method of making which may be used on contaminated open wounds and tissue, dermal wound sites and/or lesions of living organisms such as animals and humans.

Another object of this invention is to provide an improved disinfectant and the method of making which may be used on exposed surfaces in food processing plants, residential, hospital, restaurants, public facilities and the like.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

A specific embodiment of the present invention is described and shown in the attached Detailed Description. For the purpose of summarizing the invention, the invention relates to an improved non-toxic environmentally friendly aqueous disinfectant for use as a prevention against contamination by potentially pathogenic bacteria, virus and fungi. The improved aqueous disinfectant is suitable for use on exposed surfaces. In addition, the improved aqueous disinfectant is suitable for use on dermal wound sites and lesions of living organisms such as animals and humans. The aqueous disinfectant is pH neutral.

The improved aqueous disinfectant comprises an aqueous solution of silver citrate wherein the silver is electrolytically generated in a solution of citric acid and water. The electrolytically generated silver forms an organic metal complex with the citric acid such as a chelated organic metal complex with the citric acid. In one example of the invention, the solution of citric acid and water comprises approximately 5.0% to 10.0% citric acid by volume. The silver citrate formed by the electrolytically generated silver has a concentration in excess of 0.0005% by volume.

In another example of the invention, the invention is incorporated into an aqueous disinfectant in a concentrated form having an extended shelf-life comprising an aqueous solution of silver citrate wherein the silver is electrolytically generated in a solution of citric acid in water. The electrolytically generated silver has a concentration of in excess of 0.05% by volume.

The aqueous disinfectant may be combined with an alcohol such as ethyl alcohol (ETOH) and/or a detergent such as sodium dodecyl sulfate.

The invention is also incorporated into the process of making the disinfectant comprising the step of electrolytically generating silver in a solution of citric acid and water to formed an aqueous solution of silver citrate. The process may include creating a solution of approximately 5.0% to 10% citric acid in water by volume. A positive silver electrode is spaced relative to a negative electrode for enabling the solution to be located therebetween. A potential difference is applied to the positive and negative electrodes to establish a flow of silver ions between the positive and negative electrodes for enabling the silver ions to react with the citric acid to form silver citrate thereby.

The invention is also incorporated into the process of making silver citrate, comprising the step of electrolytically generating silver in a solution of citric acid and water to formed an aqueous solution of silver citrate.

The foregoing has outlined rather broadly the more pertinent and important features of the present invention in order that the detailed description that follows may be better understood so that the present contribution to the art can be more fully appreciated. Additional features of the invention will be described hereinafter which form the subject of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 5 is a table illustrating the shelf-life tests for initial sampling intervals;

FIG. 6 is a table illustrating the shelf-life tests for secondary sampling intervals;

FIG. 7 is a table illustrating the efficacy tests against *salmonella cholerasuis*;

FIG. 8 is a table illustrating the efficacy tests against *staphylococcus aureus*; and FIG. 9 is a table illustrating the efficacy tests against *pseudomonas aeruginosa*.

Similar reference characters refer to similar parts throughout the several Figures of the drawings.

DETAILED DISCUSSION

Process of Making

Figure 1:
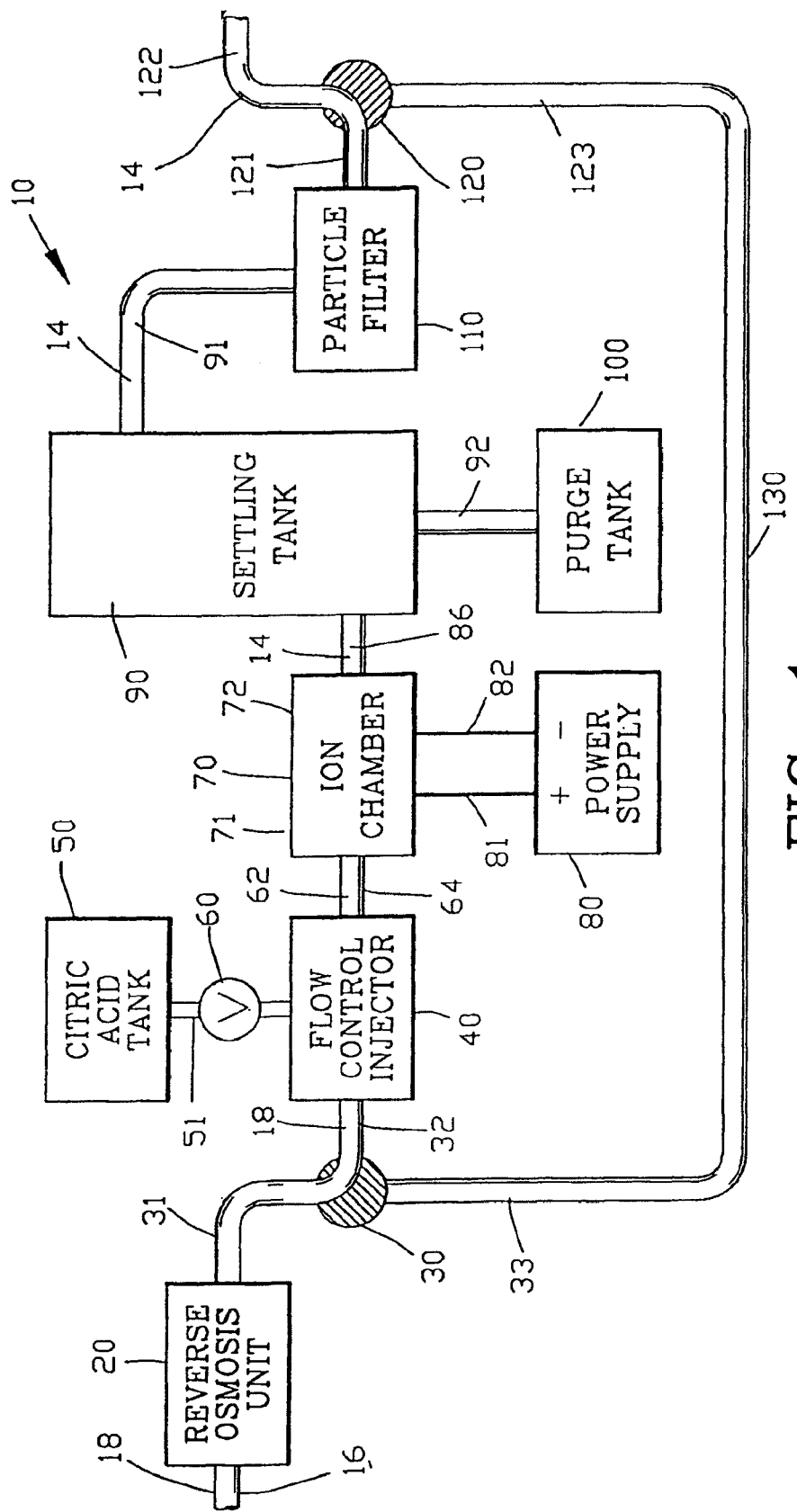
FIG. 1 is a diagram of a first process of making the disinfectant of the present invention.

FIG. 1 is a diagram of a first process 10 of making the disinfectant 14 of the present invention. The first process 10 is shown as a continuous process of making the disinfectant 14. It should be understood that the first process 10 of FIG. 1 is only an example of a process and numerous other variations and/or processes may be utilized to make the disinfectant 14 of the present invention.

The disinfectant 14 may be used immediately for any suitable application such as a disinfectant in a water system including cooling towers, hot water systems, potable water systems, or any other suitable application or surface.

The first process 10 comprises a water input conduit 16 for introducing water 18 from a water source (not shown) to a water treatment unit shown as a reverse osmosis unit 20. The reverse osmosis unit 20 passes the water 18 from the water input conduit 16 through a semipermeable membrane (not shown) for removing impurities from the water. Although the water treatment unit is shown as a reverse osmosis unit 20 it should be understood that various water treatment units may be employed within the process shown in FIG. 1. Preferably, the water 18 emanating from the reverse osmosis unit 20 is deionized medically pure water.

The water 18 emanating from the reverse osmosis unit 20 is directed to a valve 30 through a conduit 31. The valve 30 directs the water 18 though a conduit 32 to a flow control injector 40. A citric acid tank 50 contains concentrated citric acid. The concentrated citric acid is directed by a conduit 51 to a metering valve 60 for metering the concentrated citric acid into the flow control injector 40. The flow control injector 40 mixes the concentrated citric acid with the water 18 to provide a dilute citric acid solution 62. The metering valve 60 controls the concentration of the citric acid within the water 18. The diluted citric acid solution 62 is directed by a conduit 62 into an ion chamber 70.

Figure 3:
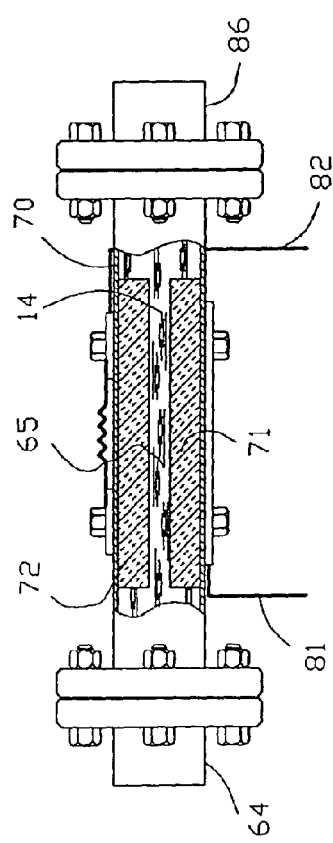
FIG. 3 is an enlarged detailed view of the ion chamber of FIGS. 1 and 2.

FIG. 3 is an enlarged detailed view of the ion chamber 70 of FIG. 1. The ion chamber 70 includes a positive and a negative electrode 71 and 72. The positive and negative electrodes 71 and 72 are located in a spaced apart position for enabling the diluted citric acid solution 62 to pass between the positive and negative electrodes 71 and 72. Each of the positive and negative electrodes 71 and 72 is fabricated from elemental silver. Preferably, the positive and negative electrodes 71 and 72 are formed from 99.9999% pure elemental silver.

A direct current power supply 80 includes a positive and a negative conductor 81 and 82 connected to the positive and negative electrodes 71 and 72. The positive and negative electrodes 71 and 72 are spaced apart a suitable distance such as 2.0 to 8.0 centimeters to allow an ionic current flow between the positive and negative electrodes 71 and 72.

Upon energizing the direct current power supply 80, an ion current flows between the positive and negative electrodes 71 and 72. The direct ion current flow between the positive and negative electrodes 71 and 72 produces electrolytically free silver ions within the diluted citric acid solution 62. The silver ions react with the citric acid in the diluted citric acid solution 62 to produce the disinfectant 14 of the present invention.

The disinfectant 14 is directed by a conduit 86 to a settling tank 90. The settling tank 90 includes an overflow conduit 91 and a drain conduit 92. The disinfectant 14 exits the settling tank 90 through the overflow conduit 91. Any precipitated materials from the disinfectant 14 within the settling tank 90 fall to the bottom of the settling tank 90. The precipitated materials at the bottom of the settling tank 90 may be removed through the drain conduit 92 to a purge tank 100. The precipitated materials in the purge tank 100 may be recycled.

The disinfectant 14 exiting through the overflow conduit 91 from the settling tank 90 is directed to a particle filter 110. Although the particle filter 110 may be any suitable filter, preferably the particle filter 110 is a submicron filter. The filtered disinfectant 14 is directed to a valve 120 by a conduit 121. The valve 120 directs the filtered disinfectant 14 to a conduit 122 for discharge from the first process 10.

The filtered disinfectant 14 discharged from conduit 122 may be used immediately for any suitable application such as a disinfectant in a water system or any other suitable application. In the event a greater concentration of the disinfectant 14 is desired, the disinfectant 14 may be recirculated for increasing the concentration of the disinfectant 14.

Figure 2:
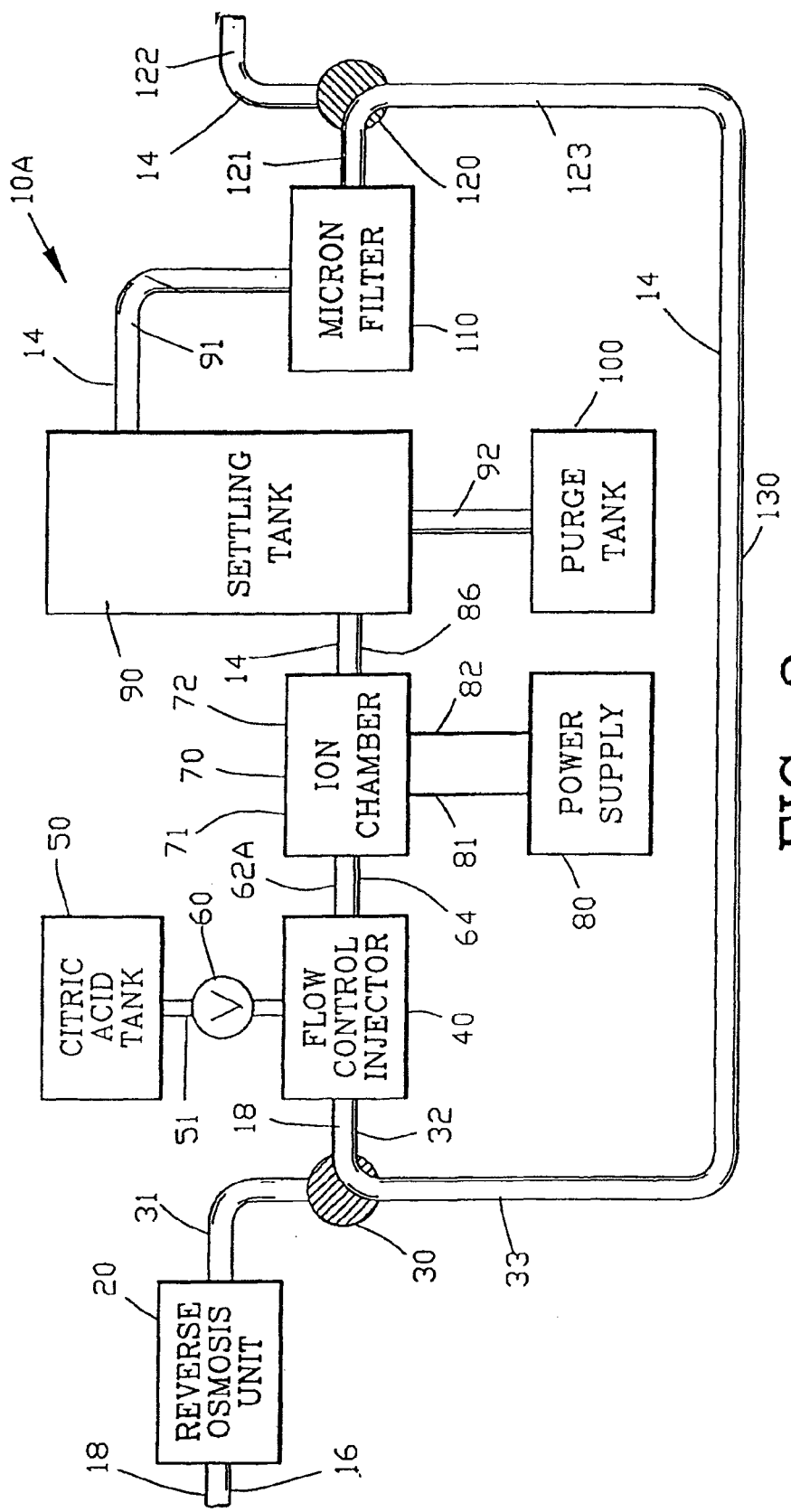
FIG. 2 is a diagram of a second process of making the disinfectant of the present invention.

FIG. 2 is a diagram of a second process 10A of making the disinfectant 14 of the present in a concentrated form. The second process 10A is shown as a recirculating process of making the disinfectant 14 and for increasing the concentration of the disinfectant 14. In the concentrated form, the disinfectant 14 may be bottled for use at a later time. It should be understood that the second process 10A of FIG. 2 is only an example of a process and numerous other variations and/or processes may be utilized to make the disinfectant 14 of the present invention.

In the second process 10A shown in FIG. 2, the valve 30 and 120 are move into positions opposite to the positions shown in FIG. 1. The valve 120 directs the filtered disinfectant 14 to a conduit 123. The conduit 123 is connected through a conduit 130 to the conduit 32 of the valve 30.

The valve 30 directs the filtered disinfectant 14 though the conduit 32 to the flow control injector 40. Additional concentrated citric acid is directed through the metering valve 60 into the flow control injector 40. The flow control injector 40 mixes the concentrated citric acid with the filtered disinfectant 14 to increase the concentration of the citric acid solution 62A.

The citric acid solution 62A is directed into an ion chamber 70 to produce additional silver ions within the citric acid solution 62A. The silver ions react with the citric acid in the citric acid solution 62A to increase the concentration of the disinfectant 14. The disinfectant 14 is passed through the settling tank 90 to exit through the overflow conduit 91. The disinfectant 14 is filtered by the particle filter 110 and is directed to the valve 120 by the conduit 121.

The valve 30 and 120 are maintained in positions shown in FIG. 2 to continue to recirculate the disinfectant 14 for increasing the concentration of the disinfectant 14. Upon obtaining the desired concentration of the disinfectant 14, the valve 120 may be moved to the position shown in FIG. 1 to discharge the disinfectant 14 from the conduit 122.

Figure 4:
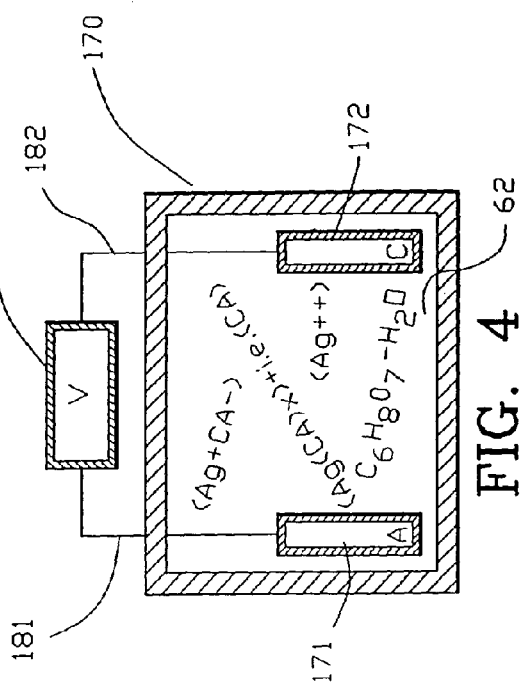
FIG. 4 is an enlarged detailed view of an ion chamber suitable for making the disinfectant of the present invention in a batch process.

FIG. 4 is an enlarged detailed view of an ion chamber 170 suitable for making the disinfectant of the present invention in a batch process. The ion chamber 170 includes a positive and a negative electrode 171 and 172. Each of the positive and negative electrodes 171 and 172 is fabricated from 99.9999% pure elemental silver.

The positive and negative electrodes 171 and 172 are located in a spaced apart position for enabling the citric acid solution 162 to pass between the positive and negative electrodes 171 and 172. Preferably, the positive silver electrode 171 is spaced relative to a negative electrode 172 a distance sufficient to enable silver ion flow therebetween. The spacing of the positive and negative electrodes 171 and 172 has been shown in an exaggerated fashion in FIG. 4. Preferably, a spacing of approximately 2.0 to 8.0 mm. has been found to be suitable for the above concentration of citric acid and water.

A direct current power supply 180 includes a positive and a negative conductor 181 and 182 connected to the positive and negative electrodes 171 and 172. Upon energizing the direct current power supply 180, an ion current flows between the positive and negative electrodes 171 and 172. The direct ion current flow between the positive and negative electrodes 171 and 172 produces electrolytically free silver ions within the citric acid solution 162. The silver ions react with the citric acid in the citric acid solution 162 to produce the disinfectant 14 of the present invention.

The process of making a disinfectant comprises electrolytically generating silver ions in a solution of citric acid and water to form an aqueous solution of silver citrate. Preferably, the solution of citric acid and water comprises a solution of approximately 5.0% to 10% citric acid in water by volume. A potential difference of 12 volts to 50 volts provides a flow of silver ions in the range of 0.1 amperes to 0.5 amperes per square inch. A more fuller explanation of the content of the solution within the ion chamber 170 will be described in greater detail hereinafter.

The prior art has established in that the generation of both silver ions and copper ion in water provides the best disinfectant properties. The combination of silver ions and copper ions provides superior disinfecting properties than either silver ions alone or copper ions alone. This synergistic effect of silver ions and copper ions in water has been well established by the prior art.

In contrast to this established prior art, the disinfectant of the present invention is formed in a solution of citric acid and water rather than water alone. Additionally, the disinfectant of the present invention has superior properties with only silver ions alone rather than the combination of both silver ions and copper ions. The silver ions of the present process react with the citric acid to form a silver citrate. The silver citrate provides superior disinfectant properties over the prior art process of generating silver and copper ions in water.

In further contrast to the established prior art, the disinfectant of the present invention has a stable ionic form having an extended useful shelf-life. The useable shelf-life of the disinfectant of the present invention enables the aqueous disinfectant solution to be packaged in an aqueous concentrate form.

Composition

The improved disinfectant is an aqueous solution of silver citrate wherein the silver is electrolytically generated in a solution of citric acid and water. The silver citrate formed in accordance with the above process has different characteristics than other forms of silver citrate.

Concentrations of 0.1% silver citrate by volume have been formulated in accordance with the above process. A concentration of 0.1% silver citrate by volume corresponds to 1000 parts per million (ppm). The concentration of 0.1% silver citrate was formed in a solution of citric acid and water comprises approximately 10.0% citric acid by volume. Higher concentration of the silver citrate are believed to be obtainable by the above process. It appears the higher the concentration of citric acid in water, the higher the concentration of silver citrate formed by the above process.

The Merck Index, Eleventh Edition (1989) page 1348 states that silver citrate is soluble in 3500 parts water. A concentration of 1 to 3500 corresponds to 285 parts per million (ppm). Obviously, the silver citrate formed in accordance with the above process has different solubility than other forms of silver citrate.

Nuclear magnetic resonance tests (1H NMR) were preformed on the silver citrate formed in accordance with the above process and a blank citric acid sample. The samples showed an overwhelming excess of citric acid, with little or no other anions present. It is postulated the Ag must be in the form of the cation $Ag+$ complexed with the citric acid. It is theorized the empty 5 s orbital of $Ag+$ overlaps with the delocalized $\pi$ bond on one of the carboxyl groups of citric acid. The citric acid anion is the counterion for this complex ion $(Ag(CA)x)+$I.e. (CA). CA is citric acid or is $(C_6H_8O_7-H_2O)$. Another possibility is a zwitterion, where the negative charge is on the complex itself, $(Ag+CA-)$ where the total charge of the complex is neutral. Either or both of these species may exist in the silver citrate formed in accordance with the above process. Multiple complexation to $Ag+$ is also possible.

A second formulation of the improved disinfectant of the present invention includes the addition of an alcohol. In one example of the second formulation of the improved disinfectant, ethyl alcohol (ETOH) is added in an approximate amount of 20% by volume. However, it should be understood that other types of alcohols may be added to the second formulation of the improved disinfectant of the present invention.

A third formulation of the improved disinfectant of the present invention includes the addition of a detergent. In one example of the third formulation of the improved disinfectant, sodium dodecyl sulfate is added in an approximate amount of 0.1% by volume.

Shelf-Life Study

The copper and silver ions in the prior art aqueous solution have only a limited stable ionic life. After a limited time, the copper and silver ions in the prior art aqueous solution form complexes with other elements thus diminishing the concentration of the copper and silver ions within the aqueous solution.

A significant difference of the disinfectant of the present invention is the stable life of the silver citrate. The present invention provides an aqueous disinfectant solution having a stable ionic form having an extended useful shelf-life. The extended useful shelf-life of the disinfectant of the present invention enables the disinfectant to be packaged in an aqueous concentrate form.

A series of tests was preformed on the following formulations.

1. Silver and Citric Acid (1.0% citric acid solution/pH 6.0)
2. Silver and Citric Acid (5.0% citric acid solution/pH 6.0)
3. Silver and Citric Acid (10% citric acid solution/pH 6.0)

The silver and citric acid formulations were prepared using 100/100 silver:silver electrodes. The electrodes were immersed in 1.0, 5.0 and 10% citric acid solutions and a current was applied for approximately two hours. The solutions were stored for 24 hours to allow for precipitation. The solutions were filtered using #2 Whatman filter paper. The final pH was adjusted to 6.0 with sodium carbonate and sodium bicarbonate.

FIG. 5 is a table illustrating the results of the shelf-life test for the initial shelf-life sampling intervals. The initial intervals for the initial shelf-life sampling intervals of the disinfectant were 1 week, 2 weeks, 3 weeks and 4 weeks. FIG. 5 illustrates that silver citrate is not stable at high concentrations in the 1.0% citric acid solution. The 300 ppm silver citrate did not remain in the 1.0% citric acid solution. However, the 300 ppm silver citrate was stable in the 10% citric acid solution.

FIG. 6 is a table illustrating the results of the shelf-life test for secondary shelf-life sampling intervals. The secondary intervals for the secondary shelf-life sampling intervals of the disinfectant were 0 weeks, 7 weeks, 14 weeks and 21 weeks. FIG. 6 also illustrates that silver citrate is not stable at high concentrations in the 1.0% citric acid solution. Conversely, the silver citrate was stable in both the 5% and 10% citric acid solutions.

The results seen in FIG. 6 for week 21 confirm the stability of the silver citrate in the 5.0% and 10% citric acid solutions. The stability of the silver citrate in the 1.0% citric acid solution experienced significant reductions during the last phase of the study. The minimum concentration of the citric acid solution is therefore some value greater than 1.0% and less than 5.0%. The maximum concentration of the citric acid in the aqueous solution has not been determined by test. However, it is believed that the maximum concentration of the citric acid in the aqueous solution much greater than 10.0%. It is also evident from these results, that the higher the concentration of the citric acid in the aqueous solution, the greater the concentration of silver ions that can be stabilized.

Laboratory Study

In order to establish the effectiveness of the improved disinfectant of the present invention, laboratory tests were performed against various test microorganisms. The test microorganisms considered were (a) *pseudomonas aeruginosa* strain ATCC 15442, (b) *Salmonella cholerasuis* strain ATCC 10708 and (c) *Staphylococcus aureus* strain ATCC 6538.

The inoculum level for each of the test microorganisms were established in a similar manner. Test strains were grown individually at 35° C. for 24 hr. The cells were harvested by centrifugation at 10,000×g for 10 minutes and washed twice with Butterfield's Phosphate Buffer (BPB of pH 7.2). The cells were resuspended in the Butterfield's Phosphate Buffer to obtain a cell suspension of approximately $1.0 \times 10^8$ CFU/mL for each microorganism (target inoculum levels were approx. $10^6$ in the final test solution).

The test microorganisms considered were tested at uniform sampling intervals, The sampling intervals selected were (a) 15 seconds (ethanol trials only), (b) 1 minute, (c) 5 minutes, (d) 10 minutes and (e) 30 minutes.

Five compounds were tested against the test microorganisms. The five compounds tested were (a) silver and citric acid (4.27 ppm in a 0.1% citric acid solution), (b) copper and citric acid (4.07 ppm in a 0.1% citric acid solution), (c) citric acid (0.1% citric acid solution), (d) silver (4.08 ppm), citric acid (0.1%) and ethanol (20%) and (e) Ethanol (20%).

The silver and citric acid (4.27 ppm in a 0.1% citric acid solution) was prepared using 100/100 silver:silver electrodes. The electrodes were immersed in a 0.1% citric acid solution and current was applied for approximately two hours. The solution was stored for 24 hours to allow for precipitation. The solution was filtered using No. 2 Whatman filter paper. The final pH was adjusted to 7.0. The concentration tested had a silver concentration of 4.27 mg/L.

The copper and citric acid (4.07 ppm in a 0.1% citric acid solution) was prepared using 100/100 copper:copper electrodes. The electrodes were immersed in a 0.1% citric acid solution and current was applied for approximately two hours. The solution was stored for 24 hours to allow for precipitation. The solution was filtered using #2 Whatman Filter paper. The final pH was adjusted to 7.0. The concentration tested had a copper concentration of 4.07 mg/L (as measured by ICAP).

The citric acid (0.1% citric acid solution) was prepared using deionized water. The pH was adjusted to 7.0.

The silver (4.08 ppm), citric Acid (0.1%) and ethanol (20%) was prepared using 100/100 silver:silver electrodes. The electrodes were immersed in a 0.1% citric acid solution and current was applied for approximately two hours. The solution was stored for 24 hours to allow for precipitation. The solution was filtered using #2 Whatman filter paper. The final pH was adjusted to 7.0. The solution was diluted with ethanol to yield a concentration of 4.08 mg/L silver in a 20% ethanol solution.

The Ethanol (20%) was prepared with by diluting Reagent grade ethanol with deionized water to make the appropriate dilution.

The test microorganisms were tested in accordance with the following test procedures. Duplicate trials were conducted for each test variable. Ninety nine volumes of the test solutions in 250 mL Erlenmeyer flasks were prepared from sterilized deionized water. The solutions were inoculated separately with one mL of 24 hour culture from each of the test strains to yield a flask inoculum level of approximately $1.0 \times 10^6$ CFU/mL. The actual count for each of the microorganisms are set forth in FIGS. 7-9.

Solutions were mixed well and kept under constant agitation. Samples of 1.0 mL were removed at the above specified time intervals and placed into 9.0 mL Neutralization Broth media (Difco) to yield an initial dilution of 1:10. All samples were serially diluted in the Butterfield's Phosphate Buffer solution (BPB) and plated onto Tryptic Soy Agar (TSA) in duplicate using the pour plate technique. Percent reductions were calculated for each test solution against each test strain.

The results of the laboratory study can be seen in FIGS. 7-9. For all tests which utilized either copper or silver ions, concentrated solutions were prepared 24 hours prior to the beginning of the study. Solutions were filtered and determinations for ion content were made. From these stock solutions (copper ion concentration as measured by ICAP and silver ion concentration as measured by Atomic Absorption analysis), final working solutions were made. The target ion concentration for both copper and silver was 5.0 mg/L.

FIG. 7 is a table illustrating the efficacy tests against *salmonella cholerasuis*. The trials that utilized 20% ethanol showed a slow, but complete disinfection. The ethanol solution has an approximate 1.0 $\log_{10}$ reduction after one minute. Near complete disinfection was seen after 30 minutes of contact time. Of the three organisms tested, *salmonella cholerasuis* was the one most effected by the ethanol disinfectant. The copper:citric acid was not effective in disinfecting *salmonella cholerasuis* at any of time periods. The citric acid solution was slightly more effective in reducing the number of *salmonella cholerasuis*, achieving a 1.0 $\log_{10}$ reduction at the 30 minute time period. Both silver:citric acid and silver:citric acid with ethanol exhibited a 6.0 $\log_{10}$ reduction over the course of the 30 minute trial. The silver:citric acid solution showed a 5.0 $\log_{10}$ reduction within the first 5 minutes and a greater 6.0 $\log_{10}$ reduction at the 10 minute time period. Silver:citric acid with ethanol appeared to be the most effective, exhibiting a 2.36 $\log_{10}$ reduction within in the first minute and a greater than 6.0 $\log_{10}$ reduction within the first 5 minutes of contact.

FIG. 8 is a table illustrating the efficacy tests against *staphylococcus aureus*. This table indicates a different reaction for the 20% ethanol against *staphylococcus aureus* as compared to *salmonella cholerasuis*. No significant reduction was seen between 15 seconds and 30 minutes. Neither citric acid nor copper:citric acid was effective against *staphylococcus aureus*. Neither of the aforementioned formulas were able to significantly reduce the number of *staphylococcus aureus* organisms present within the 30 minute time period. However, both silver:citric acid and silver:citric acid with ethanol exhibited a 6.0 $\log_{10}$ reduction over the course of the 30 minute trial. The silver:citric acid solution showed a 3.0 $\log_{10}$ reduction within the first 10 minutes and a greater than 6.0 $\log_{10}$ reduction at the end of 30 minutes. Silver:citric acid with ethanol appeared to be the most effective, exhibiting a 2.36 $\log_{10}$ reduction within the first minute and a greater than 6.0 $\log_{10}$ reduction within the first 5 minutes of contact.

FIG. 9 is a table illustrating the efficacy tests against *pseudomonas aeruginosa*. The seen in this table for *pseudomonas aeruginosa*, indicate similar results as those seen for that used *staphylococcus aureus*. For the 20% ethanol trials, no significant reduction was seen between 15 seconds and 30 minutes. This same trend was recorded for citric acid and copper:citric acid. Both silver:citric acid and silver:citric acid with ethanol exhibited near or greater than 6.0 $\log_{10}$ reductions over the course of the 30 minute trial. The silver:citric acid solution showed a 2.49 $\log_{10}$ reduction at the 10 minute time period and a greater than 5.70 $\log_{10}$ reduction at the end of 30 minutes. Silver citric acid with ethanol showed the best disinfection against *pseudomonas aeruginosa*, mirroring the results seen with the other two organisms. A greater than 6.0 $\log_{10}$ reduction was recorded at the 5 minute sampling period.

Field Trial Results

The improved disinfectant has been tested in preliminary veterinary field trials to establish the effectiveness of the present invention. The veterinary field trial test were conducted by licensed veterinarians on equine species. The improved disinfectant was tested on contaminated open, non-healing tissue and wounds. The open, non-healing wounds were treated with wet dressings or by spraying the improved disinfectant onto the wound.

The disinfectant has been tested on dermal lesions both contaminated and infected with gram negative and gram positive bacteria. The results have shown that this formulation exhibits superior performance as compared to available disinfectant products currently on the market. The disinfectant formulation has shown to be very efficacious for irrigating deep wounds and abscesses without damage to tissue. Decreased healing time and reduction in scar formation have been observed repeatedly during the study. The disinfectant appears to promote healthy granulation without excessive fibrosis.

The disinfectant has been used as a surface disinfectant and therefore has shown best results with extended contact with the contaminated tissue. On surface wounds, best results are obtained with "wet dressing" or frequent spray applications for dermal surfaces not amenable to applied dressing. Drained abscesses are flushed, the disinfectant solution is held in the cyst, then drained and again filled and agitated for 2-3 minutes before allowing to drain. Deep wounds closed with drains have shown rapid healing time and reduced draining when flushed with the disinfectant. An additional use for the disinfectant may be as a uterine flush for bacterial and/or fungal/yeast infection. Preliminary results with this application have shown to be very promising.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An aqueous solution comprising greater than 5% wt/vol citric acid, a disinfectant amount of a complex having the formula $Ag^+CA^-$, wherein $CA^-$ is the citric acid anion, $C_6H_7O_7^-$, and an alcohol, a detergent or a mixture thereof.

2. The aqueous solution of claim 1, comprising greater than 10% wt/vol citric acid.

3. The aqueous solution of claim 1, which contains an alcohol.

4. The aqueous solution of claim 3, wherein the alcohol is ethanol.

5. The aqueous solution of claim 1, which contains a detergent.

6. The aqueous solution of claim 5, wherein the detergent is sodium dodecyl sulfate.

7. The aqueous solution of claim 1, which contains both a detergent and an alcohol.

8. The aqueous solution of claim 7, wherein the detergent is sodium dodecyl sulfate.

* * * * *